United States Patent [19]

Holst et al.

[11] 4,066,828

[45] Jan. 3, 1978

[54] PROCESS FOR THE PRODUCTION OF WATER-ADSORBING CELLULOSE ETHERS

[75] Inventors: Arno Holst; Helmut Lask; Michael Kostrzewa, all of Wiesbaden, Germany

[73] Assignee: Hoechst Aktiengesellschaft, Germany

[21] Appl. No.: 683,967

[22] Filed: May 6, 1976

[30] Foreign Application Priority Data

May 7, 1975  Germany .................................. 2520337

[51] Int. Cl.$^2$ ..................... C08B 11/00; C08B 11/20; C08B 11/193; C08B 15/10
[52] U.S. Cl. ..................................... 536/87; 128/296; 260/17 A; 536/84; 536/88
[58] Field of Search ................. 260/17 A; 536/84, 87, 536/88

[56] References Cited

U.S. PATENT DOCUMENTS

| | | | |
|---|---|---|---|
| 1,884,629 | 10/1932 | Dreyfus ................................... | 536/98 |
| 2,517,577 | 8/1950 | Klug et al. .............................. | 536/98 |
| 2,667,480 | 1/1954 | Branon et al. .......................... | 536/98 |
| 3,069,409 | 12/1962 | Henry et al. ............................ | 536/98 |
| 3,085,087 | 4/1963 | Henry et al. ............................ | 536/98 |
| 3,589,364 | 6/1971 | Dean et al. ............................. | 128/284 |
| 3,936,441 | 2/1976 | Holst et al. ............................. | 536/98 |
| 3,965,091 | 6/1976 | Holst et al. ............................. | 536/98 |

OTHER PUBLICATIONS

"The New Cellulose Solvent: Dimethyl Sulfoxide--Paraformaldehyde", Johnson et al., 39th Executive Conference, The Institute of Paper Chemistry, Appleton, Wisconsin, May 8, 1975, pp. 78–80, 82 & 83.

Primary Examiner—Ronald W. Griffin
Attorney, Agent, or Firm—James E. Bryan

[57] ABSTRACT

This invention relates to an improvement in the process for the production of water-adsorbing, but at least partially water-insoluble, cellulose ethers in which cellulose is alkalized in a liquid reaction medium and etherified in a manner such that by etherification only an at least largely water-soluble carboxymethyl cellulose, carboxymethyl hydroxyethyl cellulose, hydroxyethyl cellulose or methyl hydroxyethyl cellulose is produced, and in which the cellulose is reacted in an alkaline reaction medium before, during, or after the etherification with a cross-linking agent which is polyfunctional towards cellulose and selected from the group consisting of acrylamido methylene chloroacetamide, dichloroacetic acid, phosphorous oxychloride, or a compound in which at least two groups functional towards cellulose are the acrylamido group 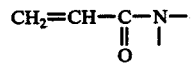

the chloroazomethine group 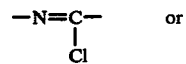 or the allyloxy azomethine group 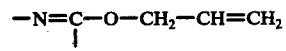

the improvement comprising effecting alkalization, etherification, and cross-linking in a liquid reaction medium other than isopropyl alcohol.

3 Claims, No Drawings

PROCESS FOR THE PRODUCTION OF WATER-ADSORBING CELLULOSE ETHERS

The present invention relates to a process for the production of water-adsorbing, but at least partially water-insoluble, cellulose ethers.

It is known, for example from U.S. Pat. No. 3,589,364, to cross-link water-soluble carboxymethyl cellulose, which can be produced by etherification of cellulose with monochloroacetic acid, in order to obtain a cellulose ether which is, at least in part, water-insoluble, but which has the capacity of adsorbing relatively large quantities of water, and of simultaneously swelling. The cross-linking may take place before, after, or simultaneously with, the etherification. Reaction agents which are polyfunctional towards cellulose are used as cross-linking agents, for example epoxy compounds, polychlorinated higher alcohols, or divinyl sulfone. Epichlorohydrin is preferably used, because it effects simultaneous cross-linking and etherification. Cross-linking takes place in the presence of a relatively small quantity of water, either in a semi-dry environment, or in the presence of relatively large quantities of an inert organic diluent, for example isopropanol present in a quantity 40 times that of the cellulose. At standard temperature cross-linking takes many hours, e.g. 18 hours; at a higher temperature the reaction is more rapid, but even at temperatures over 70° C it still requires several hours, e.g. 3.5 hours.

U.S. Pat. No. 3,936,441, having the title "Process For The Production of Water-Adsorbing Cellulose Ethers," discloses a process by means of which the above-mentioned cross-linked cellulose ethers may be obtained in a relatively short cross-linking reaction. According to this process, water-adsorbing, but largely water-insoluble, i.e., more than 50 per cent by weight water-insoluble, cellulose ethers are produced by alkalizing cellulose in the presence of alkali and isopropanol as a reaction medium, a process in which the cellulose reacts with an etherification agent in such a manner that by means of a mere etherification a water-soluble carboxymethyl cellulose, carboxymethyl hydroxyethyl cellulose, hydroxyethyl cellulose or methyl hydroxyethyl cellulose would be produced and in which the reaction takes place before, simultaneously with, or after, the etherification, with a cross-linking agent polyfunctional towards cellulose in an alkaline reaction medium. This reaction medium is either acrylamido methylene chloroacetamide, dichloroacetic acid or phosphorous oxychloride or a compound in which at least two groups functional towards cellulose are:

the acrylamido group 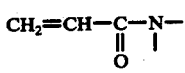

the chloroazomethine group 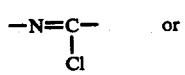 or the allyloxy azomethine group 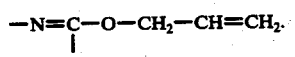

It now has been found that the above-mentioned cellulose ethers also may be obtained within a relatively short cross-linking reaction, if alkalization, etherification, and cross-linking are carried out in a liquid reaction medium other than isopropyl alcohol.

In the process according to the invention the known etherification process is used in which alkali cellulose is etherified in such a manner that a cellulose is produced which is at least largely water-soluble. For practical reasons, alkali cellulose produced from aqueous NaOH solution is used almost exclusively, but the etherifications may also be carried out with alkali cellulose produced from an aqueous KOH solution of LiOH solution. Preferred etherification agents for the production of water-soluble cellulose ethers are sodium monochloroacetate, monochloroacetic acid, methyl chloride, ethylene oxide and propylene oxide, either singly or in admixture, and ethyl chloride, especially when mixed with ethylene oxide or propylene oxide.

The process according to the invention includes an etherification reaction as well as a cross-linking reaction. The cross-linking reaction is carried out in such a manner that at least 20 per cent by weight of the cellulose ether is no longer water-soluble, but the product is swellable with water. Such an additional cross-linking reaction is also known. In the process according to this invention the above-mentioned cross-linking agents are used, for example:

methylene-bis-acrylamide,
N,N'-dimethylol(methylene-bisacrylamide),
trisacryloyl hexahydrotriazine,
acrylamido methylene chloroacetamide,
2,4,6-trichloropyrimidine,
2,4,5,6-tetrachloropyrimidine,
cyanuric chloride,
triallyl cyanurate,
dichloroacetic acid, and
phosphorous oxychloride.

Depending on the kind of cross-linking agent, 0.001 to 0.2 part by weight is used per part by weight of cellulose. An exception is dichloroacetic acid, of which at least 0.1 part by weight per part by weight of cellulose should be used. If monochloroacetic acid is used alone or together with ethylene oxide as an etherification agent, the amount of the cross-linking agent dichloroacetic acid must be relatively high compared with the quantity of monochloroacetic acid used.

If a cross-linked cellulose ether having a high water retention value (WRV) is to be obtained, an organic solvent is advantageously used as a liquid reaction medium, for example dioxane, methyl ethyl ketone, ethanol, acetone or tertiary butyl alcohol, which moreover reacts significantly with the reactants or not at all.

If water is used as a reaction medium, cross-linked cellulose ethers are obtained the water retention value of which is considerably lower than, for example only half of, that of the cross-linked cellulose ethers described in U.S. Pat. No. 3,936,441, and produced under the same conditions, but in the presence of isopropyl alcohol. In many cases of practical use this low WRV does not matter and it even may be desired. Cellulose ethers produced and cross-linked in a purely aqueous reaction medium can adsorb water very rapidly. For their production a dry alkali cellulose is preferably used, i.e. an alkali cellulose that is produced by uniformly mixing pulverized cellulose with the necessary amount of alkali by spraying with a concentrated 20 per cent aqueous alkali hydroxide solution, the alkali cellulose obtained being an almost dry powder. However, dip alkali cellulose also may be used, i.e. alkali cellulose produced by dipping cellulose plates or cellulose webs in an aqueous alkali hydroxide solution and then squeezing and shredding them. Such alkali cellulose is composed of a granular, non-agglomerating mixture. If a purely aqueous reaction medium is employed, the cross-linking preferably is not deferred until after the etherification, but is carried out simultaneously with the etherification process. In a purely aqueous reaction medium, alkylene oxides, especially ethylene oxide, react very rapidly. Thus, accumulation of heat may lead to discolored products, but this is not disadvantageous for some practical applications. Local overheating may be prevented by providing a uniform heat exchange. In mixed etherification processes, it is possible for the other etherification agent to assume the role of a heat distributor.

Similar to the hitherto known processes, the process of the present invention leads to cross-linked products which contain a certain water-soluble portion. For many purposes this does not matter, so that it is usually unnecessary to remove the water-soluble portion. In the examples below the quantity of the portion of the cross-linked cellulose is given that is soluble in pure water at 20° C.

The cross-linked cellulose ethers produced by the process of the invention may be used for various technical purposes, for example they may serve as adsorbing material in surgical and hygienic bandages, or as dehydrating agents, for example in aqueous emulsions.

In the process according to the invention, sufficiently cross-linked products are obtained within a very short time, i.e. in about one hour, at moderate temperatures, preferably up to about 80° C. Products with varying water retention values are obtained, depending upon the etherification and cross-linking conditions. Therefore, many different requirements can be met. The quantity of water retained may be extremely high and may amount, for example, to 60 times the weight of the cross-linked cellulose ether. The water adsorbed is so firmly attached to the cross-linked product that it cannot be removed therefrom, even if a centrifugal force is applied which corresponds to 2000 times the acceleration due to gravity. In the examples below reference is made to the water retention value towards pure water at 20° C, determined after the application of such a centrifugal force.

As a further advantage of the process according to the invention products are obtained which have a high water retention value relative to the quantity of cross-linking agent used. In this manner products easily may be obtained that have a water retention capacity of 5 to 60 times their own weight.

In the examples below all percentages are by weight. Alkalization, etherification and cross-linking are carried out at the temperatures given and while the reactants are thoroughly mixed. The abbreviation "WRV" means water retention value or capacity. It is given in per cent by weight, based on the dry weight of the water-insoluble portion.

EXAMPLE 1

In a reaction vessel, 100 g of cellulose are simultaneously mixed and sprayed with 91.5 g of an aqueous NaOH solution (28 per cent), and then the mixing is continued for 45 minutes at 20° C. Then, an intimate mixture of 65 g of finely pulverized sodium monochloroacetate and 0.57 g of methylene-bis(acrylamide) is added, and etherification and cross-linking are carried out simultaneously by continuing the mixing for one hour at 80° C. The product obtained is washed salt-free with 85 per cent aqueous methyl alcohol, then dissolved in acetone, extracted and dried. The product thus obtained has a WRV of 2070 and contains 23.3 per cent of water-soluble material.

EXAMPLE 2

The procedure of Example 1 is repeated, however, with the exceptions that for simultaneous etherification and cross-linking a mixture of 55 g of sodium monochloroacetate and 41.5 g of a 30 per cent aqueous solution of dimethylol-methylene-bis(acrylamide) is used and the mixing is carried out for 1 hour at 70° C.

The product is cleaned and dried as in Example 1, has a water retention value of 907, and a water-soluble portion of 18.3 per cent.

EXAMPLE 3

125 g of cellulose are sprayed with 228 g of an aqueous NaOH solution (28 per cent) in a reaction vessel and alkalized, during continuous mixing, for 45 minutes at 20° C. Then 169 g of sodium monochloroacetate are added together with 1.2 g of methylene-bis(acrylamide). Simultaneous etherification and cross-linking take place for 1 hour at 80° C. The cleaned and dried product obtained has a WRV of 12500 and a soluble portion of 65.4 per cent.

It will be obvious to those skilled in the art that many modifications may be made within the scope of the present invention without departing from the spirit thereof, and the invention includes all such modifications.

What is claimed is:

1. In the process for the production of water-adsorbing, but at least partially water-insoluble, cellulose ethers in which cellulose is alkalized in a liquid reaction medium and etherified in a manner such that by etherification only an at least largely water-soluble carboxymethyl cellulose, carboxymethyl hydroxyethyl cellulose, hydroxyethyl cellulose or methyl hydroxyethyl cellulose is produced, and in which the cellulose is reacted in an alkaline reaction medium before, during or after the etherification with a cross-linking agent which is polyfunctional towards cellulose and selected from the group consisting of acrylamido methylene chloroacetamide, dichloroacetic acid, phosphorus oxychloride, or a compound in which at least two groups functional towards cellulose are the acrylamido group 

the chlorazomethine group 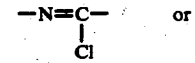 or the allyloxy azomethine group 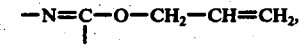

the improvement comprising effecting alkalization, etherification, and cross-linking in a liquid reaction medium selected from the group consisting of the organic solvents, dioxane, methyl ethyl ketone, ethanol, acetone and tertiary butyl alcohol, and the solvent water.

2. A process according to claim 1 including effecting alkalization, etherification, and cross-linking in a substantially pure aqueous reaction medium.

3. A process according to claim 1 including cross-linking the cellulose ether to form a cellulose ether which is more than 50 per cent by weight insoluble.

* * * * *